United States Patent [19]

Barberet et al.

[11] Patent Number: Plant 5,444

[45] Date of Patent: Apr. 23, 1985

[54] CARNATION NAMED LONFOREM

[75] Inventors: Nicole Barberet; Yves Ducloux, both of Antibes, France

[73] Assignee: Laboratoire de Physiologie Vegetale de La Londe, Antibes, France

[21] Appl. No.: 516,514

[22] Filed: Jul. 25, 1983

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new spray carnation cultivar particularly distinguished by its very light Indian Yellow flower petals marginally streaked with a Scarlet or Delft Rose color, the combination producing a very distinctive appearance due to the color contrast. These blossoms are borne on straight, relatively long, rigid peduncles branching from a rigid, upright stem having a rather abundant quantity of relatively short leaves with acute tips, the plant itself having a vigorous, upright growth habit, a profuse production of blooms and a resistance to *Fusarium oxysporum.*

1 Drawing Figure

BACKGROUND OF THE NEW PLANT

Our new carnation cultivar is the result of breeding efforts carried on by us at La Londe, Les Maures, France, since 1979 with the object of producing new carnation varieties having nice color, good quality and resistance to *Fusarium oxysporum.* This new plant originated as a seedling produced by our crossing of selected and individually identified plants growing among our stock of spray carnations maintained at La Londe for breeding purposes and this particular seedling was selected by us for propagation and test because of its very unusual color display, its very favorable growth habit and its apparent resistance to *Fusarium oxysporum.* The discovery plant was reproduced by us at La Londe, by means of cuttings, with such a favorable result with respect to retention of the novel characteristics of the original plant that we continued such propagation through several successive generations and thereby determined that the novel and distinctive characteristics of the discovery plant are fully retained from generation to generation in its reproductions and appear to be firmly fixed.

DESCRIPTION OF THE DRAWING

Our new spray carnation cultivar is illustrated by the accompanying photographic drawing which shows, in full color, the upper or flowering portion of a typical flowering stem with buds and flowers in various stages of opening, the colors shown being as nearly true to those herein specified as it is reasonably possible to obtain by conventional photographic procedures.

DESCRIPTION OF THE NEW PLANT

The following is a detailed description of our new spray carnation discovery based upon observations of greenhouse grown plants at La Londe, France, in the Spring of 1983, the color designations being specified according to The R.H.S. Colour Chart published by The Royal Horticultural Society of London, England.

THE PLANT

Origin: Seedling.

Parentage:

*Seed parent.*—Stock Plant No. 75 M R 10.

*Pollen parent.*—Stock Plant No. 419 M R. These unnamed varieties are individually identified in our permanent records and are maintained in our carnation collection for breeding purposes at La Londe, France.

Classification:

*Botanic.*—*Dianthus caryophyllus.*

*Commercial.*—Spray Carnation.

Form: A tall, erect bush having at least four stems emitted near the ground.

Height: Averaging about 107 cm. at eight months.

Main stem:

*Length.*—Less than 15 cm. due to pinching.

Branching character: Well branched.

Growth habit: Vigorous, upright and rather rigid.

Foliage:

*Quantity.*—Rather abundant.

*Number of leaves.*—At least 120.

*Leaf size.*—About 9 cm. long and 8 mm. wide, in average at the seventh node.

*Leaf shape.*—Linear with curved margin.

*Texture.*—Leathery.

*Color.*—Upper side — 189B. Under side — 189B.

*Ribs and veins.*—Hardly noticeable.

*Rachis.*—Hardly noticeable.

THE BUD

Size: Medium.

*Diameter.*—About 1.2 cm. in average.

*Length.*—About 2.7 cm. in average.

Shape: Ovoid

Color of petals:

*When sepals first divide.*—Chinese Yellow and Delft Rose.

*When petals begin to unfurl.*—Indian Yellow and Scarlet.

Sepals:

*Number.*—5 To 7.

*Shape.*—Joined at lower part with the upper portion of acute form and sharply pointed at the apex. The sepals are hooded over the bud and stand up when the flower opens.

*Color.*—Inside — Greenish white. Outside — 139C and 144C.

*Striae.*—Longitudinal.

Calyx:

*Size.*—Medium.

*Shape.*—Cylindrical and narrow.

*Aspect.*—Smooth.

Flower stem:

*Length.*—About 53 cm.

*Character.*—Erect and rather thin.

*Color.*—189A and 189B.

THE FLOWER

Blooming habit: Recurrent, blooming profusely during the midseason of Spring and Fall.

Size of bloom: Small.

*Diameter.*—Averaging about 5.1 cm.

*Depth.*—Averaging about 5 cm.

Borne: In cluster.

Shape:

*When bloom first opens.*—High centered.

*When bloom matures.*—Dome-shaped.

Petalage:

*Number of petals.*—About 28 in average.

*Arrangement.*—Imbricated.

*Form.*—Fan-shaped with serrated outer edges.

*Texture.*—Soft.

*Appearance.*—Satiny.

*Color.*—Outer Petal: Body — 19C and 43B. Base — Greenish yellow. Reverse side — 20D and 47D. Inside Petal: Body — 19C and 43B. Base — Greenish yellow. Reverse side — 20D and 47C.

Petaloids:

*Number.*—From none up to four.

*Size.*—Smaller than petals.

*Color.*—The same as petals.

Flower Stem:

*Length.*—About 53 cm.

*Character.*—Upright and of good strength.

*Color.*—189A and 189B.

Fragrance: There is fragrance present.

Persistence: The flower petals hang on and dry.

Lasting quality: As cut flower — At least ten days in vase keeping.

Disease resistance: Resistant to *Fusarium oxysporum* as observed INRA, Antibes, Alpes-Maritimes, France.

REPRODUCTIVE ORGANS

Stamens:

*Number.*—From 1 to 22.

*Arrangement.*—Encircling the pistils.

*Anthers.*—Size: Less than 4 mm. Color: Whitish.

*Filaments.*—Color — Whitish.

Pistils:

*Number.*—2 To 4.

*Styles.*—Color — Whitish.

*Stigmas.*—Color — Lightly pinkish.

Character of ovaries: Small, spherical and lightly ribbed.

This new cultivar most resembles the variety "Ministar", our new variety differing from "Ministar" by having a very vigorous first flowering, a less serrated flower petal and by its resistance to *Fusarium oxysporum.*

We claim:

1. The new and distinctive spray carnation cultivar, substantially as herein shown and described, characterized by the Indian Yellow and Scarlet coloration of its small blooms which are produced profusely on strong, straight peduncles carried on tall, upright and strong flowering stems; and by its vigorous and upright growth habit, rather abundant foliage and resistance to *Fusarium oxysporum.*

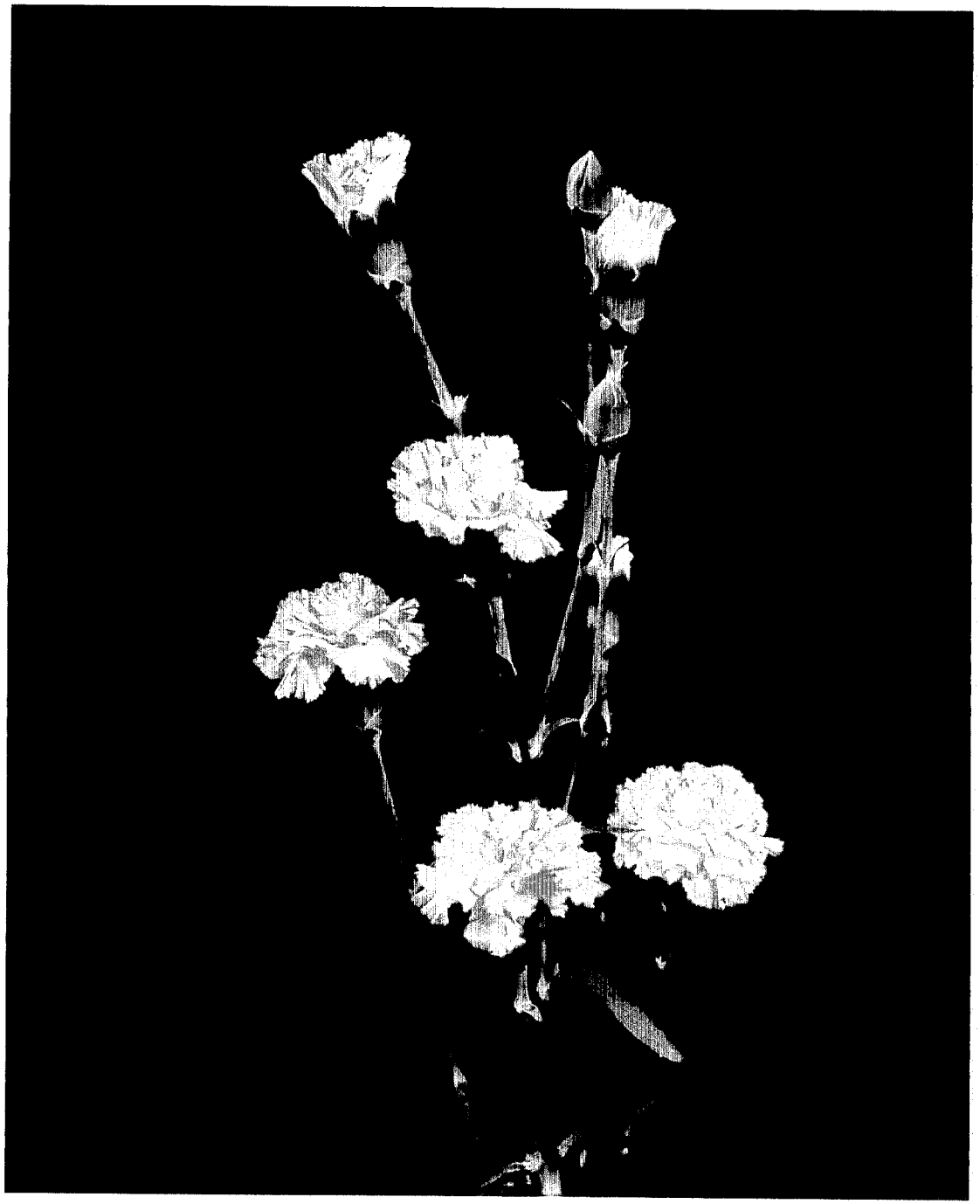

* * * * *